United States Patent [19]
Clarkson et al.

[11] Patent Number: 5,783,063
[45] Date of Patent: Jul. 21, 1998

[54] ESTIMATION OF NUCLEIC ACID

[75] Inventors: John Michael Clarkson, Bradford on Avon; Benjamin David Cobb, Holt, both of United Kingdom

[73] Assignee: Hybaid Limited, United Kingdom

[21] Appl. No.: 804,176

[22] Filed: Feb. 21, 1997

[30] Foreign Application Priority Data

Feb. 29, 1996 [GB] United Kingdom ............... 9604292.4

[51] Int. Cl.⁶ ............................................ G01N 27/26
[52] U.S. Cl. .................. 205/775; 73/64.54; 436/2; 436/89; 435/6; 435/287.2
[58] Field of Search ................. 205/775; 73/64.54; 436/2, 89; 435/6, 287.2

[56] References Cited

U.S. PATENT DOCUMENTS 5,156,810  10/1992  Ribi ..................................... 422/82.01
5,403,451  4/1995  Riviello et al. ......................... 205/775

*Primary Examiner*—Bruce F. Bell
*Attorney, Agent, or Firm*—Thomas, Kayden, Horstemeyer & Risley

[57] ABSTRACT

A method estimating a property or parameter of a nucleic acid material, which property or parameter is one to which the electrical conductivity of the nucleic acid material is related, comprises measuring the electrical conductivity of the nucleic acid material, and estimating from the measurement the property or parameter of the material by reference to a predetermined relationship between electrical conductivity and said property or parameter. This is based on the discovery that there are certain important properties of nucleic acids, the quantitative determination of which is frequently desirable, which can be assessed by measurement of the conductivity of a solution of the nucleic acid or acids. Changes in such properties may be reflected in corresponding changes of electrical conductivity. The concentration of nucleic acid in solution and the molecular weight of a species of nucleic acid are examples of important property which may be determined.

13 Claims, 5 Drawing Sheets

% RESPONSE OF DNA MOLECULES OVER A RANGE OF FREQUENCIES

DNA % RESPONSE GRADIENT VERSUS MOLECULAR WEIGHT

ESTIMATION OF NUCLEIC ACID

BACKGROUND OF THE INVENTION

This invention relates to the estimation of nucleic acid and more particularly to the estimation of a property or parameter of a nucleic acid. The invention is especially directed to the determination of concentration (quantification) of nucleic acids in solution and to the determination of molecular weight (sizing) of nucleic acid molecules.

DESCRIPTION OF THE PRIOR ART

Conventionally, DNA concentration is determined spectrophotometrically, a method which relies on the characteristic absorption of ultra-violet light (ca. 260 nm) by the nucleotide ring structure of DNA molecules. To determine molecular weight, DNA molecules are normally size-separated by agarose gel electrophoresis and then visualised using the dye ethidium bromide. DNA can also be quantified in agarose gels by comparing with known standards by measuring the fluorescence emitted following excitation by ultra-violet light (ca. 300 nm). Both methods have inherent disadvantages. UV spectrophotometers are expensive pieces of equipment requiring the use of costly quartz curvettes and rely on the 'desstructive' processing of relatively large sample volumes. The use of ethidium bromide for DNA visualisation and quantification, although a cheaper alternative, is also undesirable to its extremely toxic and carcinogenic nature.

SUMMARY OF THE INVENTION

The present invention comprises a method for the estimation of a property or parameter of a nucleic acid material, said property or parameter being one to which the electrical conductivity of the nucleic acid material is related, which method comprises measuring the electrical conductivity of the nucleic acid material, and estimating from said measurement the property or parameter of the material by reference to a predetermined relationship between electrical conductivity and said property or parameter.

The present invention is based on the discovery that there are certain important properties of nucleic acids, the quantitative determination of which is frequently desirable, which can be assessed by measurement of the conductivity of a solution of the nucleic acid or acids. Changes in such properties may be reflected in corresponding changes of electrical conductivity. The concentration of nucleic acid in solution and the molecular weight of a species of nucleic acid are examples of important property which may be determined in accordance with the present invention.

For the purposes of this invention electrical conductivity may be conveniently measured as the electrical current flowing through a solution of the nucleic acid material using electrodes of fixed surface area.

The present invention is of primary interest for the determination of properties of single species of nucleic acid. However, absolute purity of the material is not always necessary and the invention is applicable to nucleic acids containing minor amounts or other materials, including other species of nucleic acid.

DESCRIPTION OF THE DRAWINGS

An embodiment of the present invention is described below, by way of example only, with reference to the accompanying drawings, in which.

DESCRIPTION OF THE PREFERRED EMBODIMENT

Figure 1:
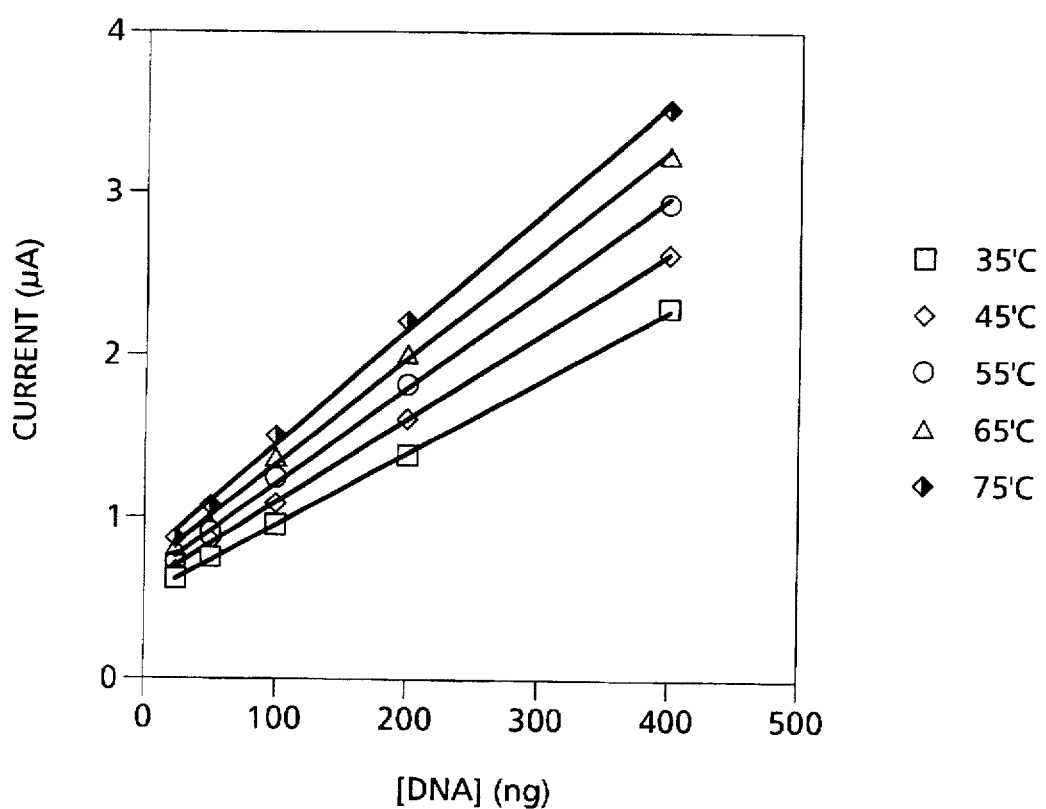
FIG. 1 is a graph of current/conductivity against DNA concentration.

The concentration of DNA may be determined by measuring the current/conductivity t a known alternating current frequency. The current recorded at any one fixed frequency has been found to be proportional to the DNA concentration. For example FIG. 1 shows how the current/conductivity recorded at 2 KHz varies with DNA concentration. This relationship applies not only to a single size of nucleic acid but is true for a range of different sized molecules. In designing apparatus for carrying out the method of this invention a conductivity meter may be readily adapted and calibrated in accordance with the predetermined relationship between current flow and concentration of nucleic acid. In practice it will usually be desirable to calibrate the instrument to deal with homogeneous DNA species but for a range of molecular weights. Thus the sample will normally first be "sized" following which the appropriate nucleic setting for concentration determination will be shown.

Figure 2:
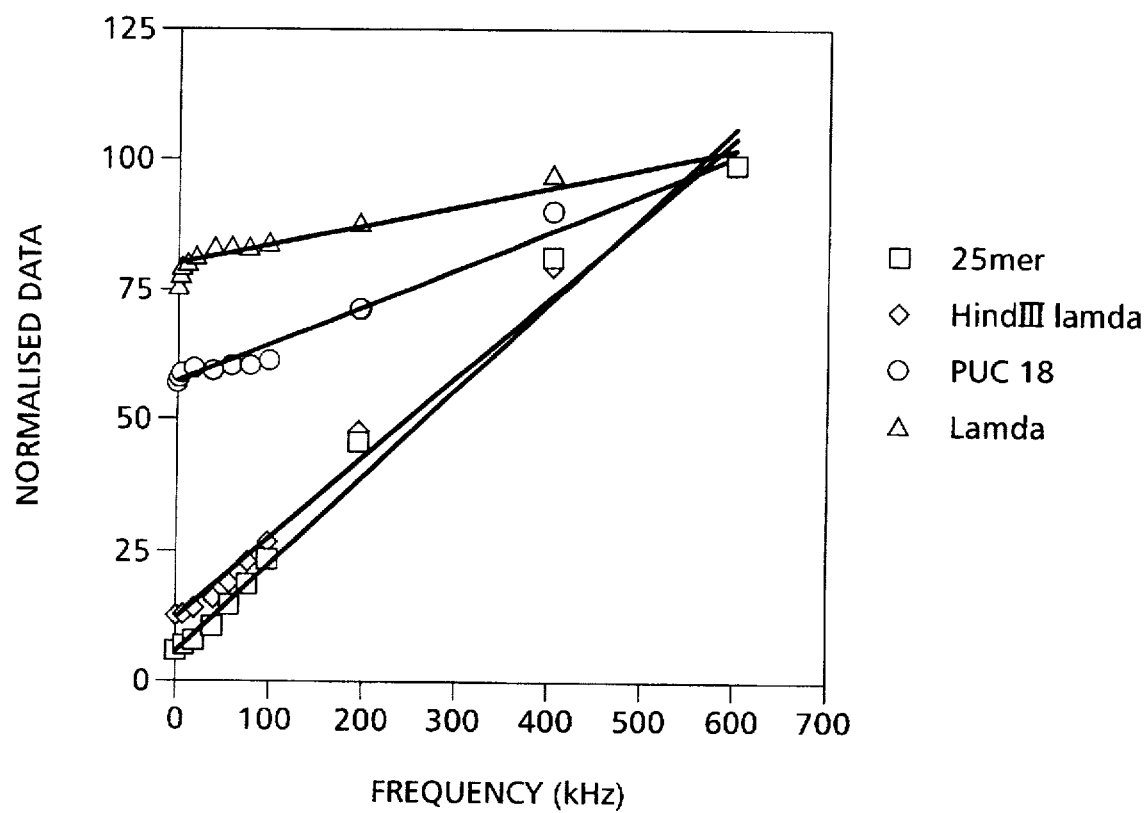
FIG. 2 is a graph of conductivity against supply frequency.

The molecular weight of DNA species is determined by the response of these molecules to varying frequencies applied across the electrodes. Plotting the current/conductivity recorded (Table 1) as percentage of the maximum current/conductivity response (% response), versus the frequency of the a.c. signal applied between the two electrodes gives characteristic curves which differ for the molecular weights of the molecules concerned (FIG. 2).

TABLE 1

| | current ($\mu$A) | | |
| --- | --- | --- | --- |
| frequency | 25 mer | puc 18 | lambda |
| 2.00E + 03 | 6 | 62 | 93 |
| 4.00E + 03 | 6 | 63 | 96 |
| 6.00E + 03 | 6 | 64 | 98 |
| 8.00E + 03 | 6 | 64 | 99 |
| 1.00E + 04 | 7 | 64 | 99 |
| 2.00E + 04 | 8 | 65 | 100 |
| 4.00E + 04 | 11 | 65 | 102 |
| 6.00E + 04 | 15 | 66 | 102 |
| 8.00E + 04 | 19 | 67 | 102 |
| 1.00E + 05 | 24 | 68 | 104 |
| 2.00E + 05 | 45 | 78 | 109 |
| 4.00E + 05 | 80 | 99 | 120 |
| 6.00E + 05 | 98 | 109 | 122 |

Figure 3:
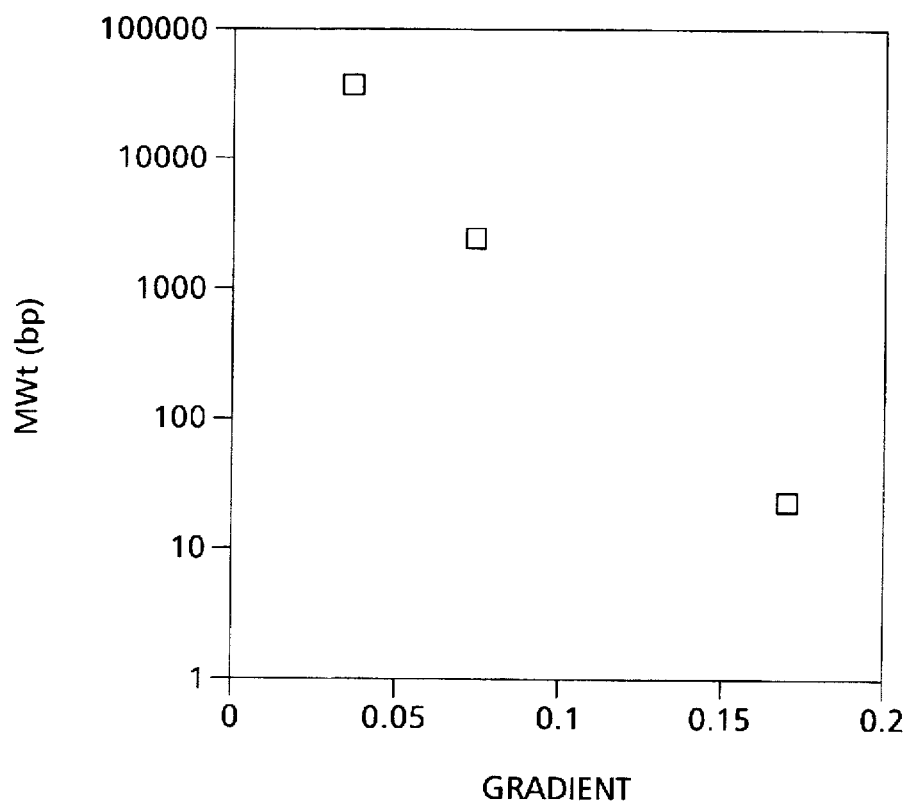
FIG. 3 is a calibration curve of log molecular weight against gradient.

For a single DNA species the molecular weight can be determined by firstly calculating the gradient of the response versus frequency curve (over the frequency range $0-5\times10^5$ Hz). The gradient value can then be compared with a calibration curve (FIG. 3) of log molecular weight plotted against gradient. For all DNA molecules tested, the gradient varies with molecular weight such that the larger the gradient value, the lower the molecular weight. The basis of this relationship is presumed to be that the mobility of the DNA molecules changes as the frequency changes; as the frequency increases, large molecules are less responsive to changes compared with smaller molecules.

Methods of DNA quantification and molecular weight determination in accordance with the invention circumvent the problem associated with the known methodologies and offer a number of distinct advantages over those conventional methods. Thus, the invention allows rapid and accurate determination of both molecular weight and concentration; it is more sensitive and accurate, is safer for the operator and it requires small sample volumes.

The characterisation of DNA outlined above has been achieved using an a.c. signal, of modulating frequency, between two thin wire platinum electrodes (alternative metals such as copper, stainless steel would also be adequate) through a solution containing DNA. Generally a fixed a.c. signal of between the two thin wire conductive electrodes. A range of frequencies of this a.c. signal, between O and 1 MHz, is applied across these electrodes and the corresponding conductivity recorded at each frequency in turn as the current passing through the solution. For example the sample DNA is dissolved in water or TE buffer in a volume of at least 10 μl. For convenience a standard 500 μl plastic tubs can be used. Two platinum thin wire electrodes are placed in the solution and connected to a function generator operating at 1 V a.c. A range of frequencies from 0–1 MHz are passed through the solution and the resulting current measured as mA using an ammeter. The DNA concentration is calculated by comparing the current passing through the solution at a frequency of 2 KHz with a standard curve (relating DNA concentration to current at a fixed frequency). Alternative frequencies can also be used.

Specific Example

Confirmation that the molecular weight of DNA molecules in solution can be determined by conductivity methods was achieved by preparing four different DNA solutions in both milli Q water and Tris EDTA (TE) buffer (25 base oligonucleotide, 700 base pair fragment, pUC 18 (=2,690 base pair) and lambda (=50,000 base pair) and a fifth solution, containing DNA of unknown molecular weight (UN). The conductivity of these solutions was measured in uA over the range of frequencies from $2 \times 10^4$ Hz to $10^5$ Hz. There was no significant difference between milli Q and TE buffer indicating that DNA molecules can be accurately sized in the most common buffer used to store DNA.

To confirm the relationship between molecular weight and conductivity, solutions were prepared in triplicate and tested. Table 2 provides this confirmation and shows that interrreplicate variation is slight. Table 3 shows the main conductivity in uA and also as a % of maximum conductivity. The main reason for expressing data in terms of % response is that although within experiment variation is low (as shown in table 1) the fragility of the current probe system causes significant variation between experiments in terms of uA readings. However the trends of conductivity changes (as expressed in % response) is consistent between experiments.

Figure 4:
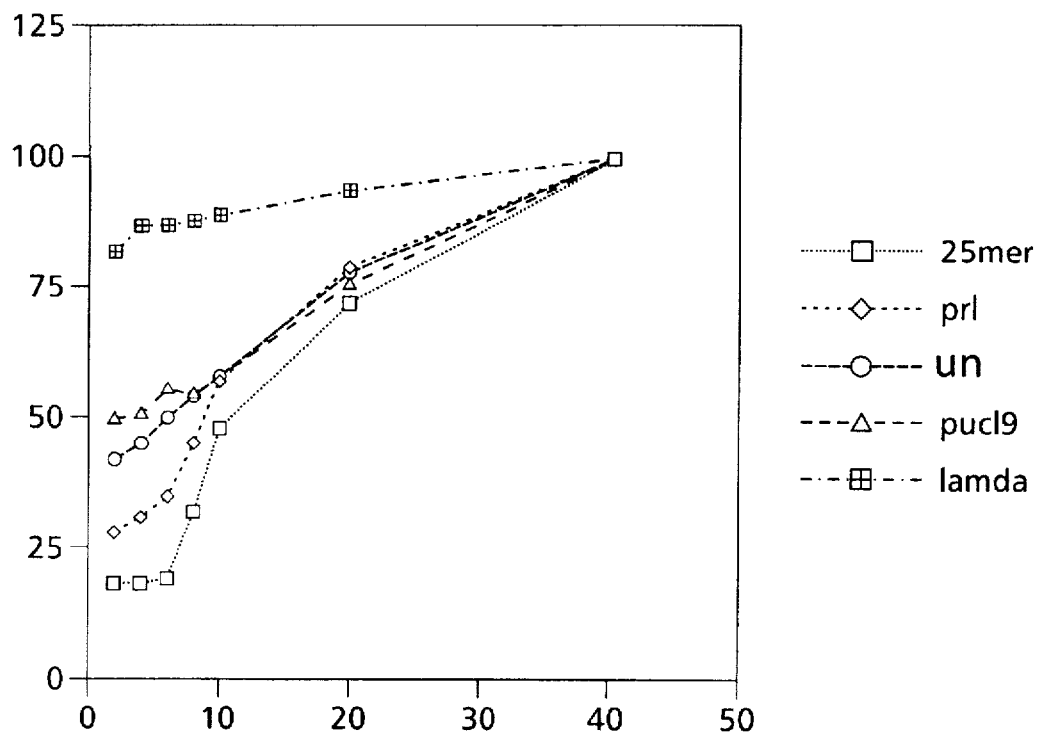
FIG. 4 is a graph of % response of DNA molecules against frequency.
Figure 5:
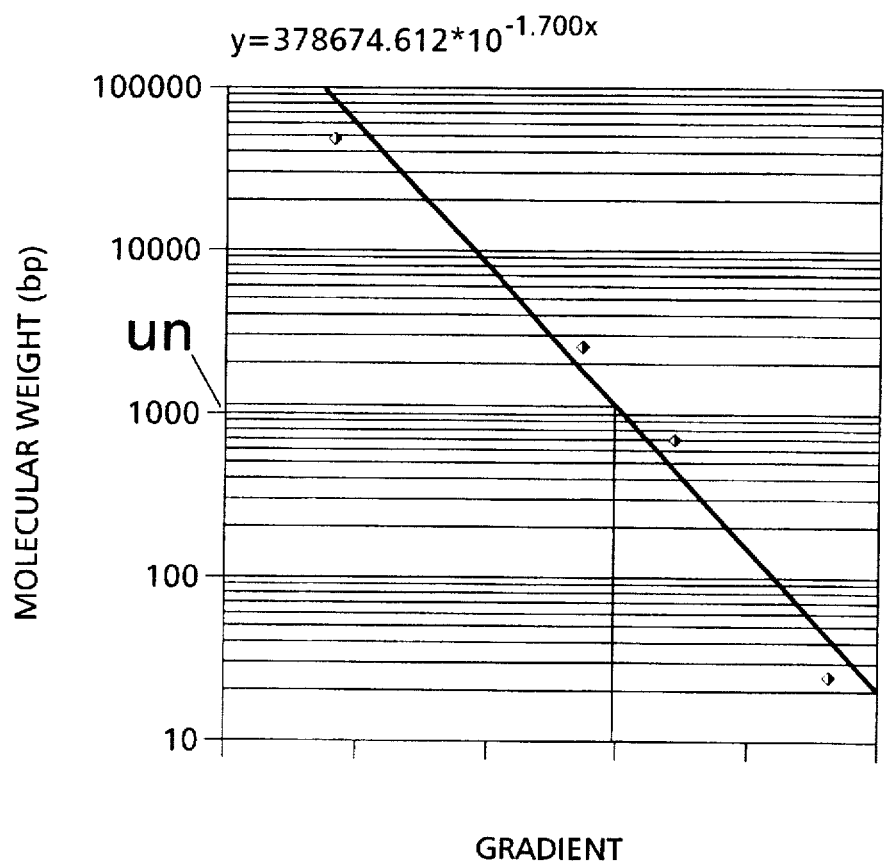
FIG. 5 is a graph of molecular weight against % response gradient.

FIG. 4 shows the mean % response data from table 3 plotted as a graph. The most obvious difference between the DNA solutions is the gradient of the slopes. When this gradient is calculated from the conductivity at $2 \times 10^4$ and $4 \times 10^5$ a near linear relationship is observed between gradient and log molecular weight (FIG. 5). Thus gradient can be used to calculate molecular weight.

The molecular weight of sample UN found from FIG. 5 is about 1047 bps, which corresponds well with estimates made from agarose gel sizing of the same fragment.

As mentioned above, the fragility of the current probe system causes significant variation between experiments. To overcoming these problems the following designs are suggested.

Production Description

The technology outlined herein is intended to form the basis of a laboratory instrument used to size and quantify nucleic acids. The instrument is based on the pipette, a tool used by all molecular biologists to accurately transfer small volumes of solutions (e.g. nucleic acids). Solutions are drawn up into disposable tips using a vacuum generated in the body of the pipette unit. The solution can then be dispensed. The DNA-Pipette has sensing electronics housed in the body of the pipette. The sensor is separate from the pipette unit and is implanted into the disposable pipette tips which may or may not be sterile. The user draws up a sample into the pipette tip. Once a suitable volume has been drawn up into the tip, the pipette can display molecular weight and concentration on the display (e.g. LCD).

The preferred sensor consists of a working electrode and a counter electrode manufactured as an interdigitated array on a suitable substrate such as silicon, glass or polycarbonate. Reference electrodes may be used but are not necessary. The electrodes may be of any suitable material. Inert metals such as platinum, gold and silver, carbon, graphite, carbonpastes and platinum inks, modified electrodes where electron transfer is mediated by electron-accepting or electron-donating compounds may also be used. Electrode geometry may include any convenient symmetry. Spherical hemispherical, disk-shaped, ring-shaped and linear electrodes which form single thin wire electrodes, interdigitated or multiple arrays of sensing units may be used. Electrodes may be of macro, micro or ultra-micro dimensions. Contact between the tip and pipette body is via an interface/contact on the barrel of the pipette.

The product described is a portable instrument. Some applications may require a stand alone instrument (e.g. where multiple samples require rapid processing). This embodiment can also be applied to other instruments which have high sample a through put. In particular microtitre plate technology allows a large number of samples to be screened using a standard plate format. This would have application in screening and diagnostics laboratories.

TABLE 2

Conductivity (μA) of DNA solutions over a range of frequencies

| replicates | | | | | |
|---|---|---|---|---|---|
| 1 | 2 | 3 | mean (μA) | frequency | size |
| 20 | 21 | 22 | 21 | 2.00E + 04 | 25 b |
| 21 | 22 | 22 | 21 | 4.00E + 04 | |
| 22 | 23 | 22 | 22 | 6.00E + 04 | |
| 35 | 35 | 36 | 36 | 8.00E + 04 | |
| 54 | 56 | 56 | 55 | 1.00E + 05 | |
| 80 | 86 | 82 | 82 | 2.00E + 05 | |
| 111 | 115 | 116 | 114 | 4.00E + 05 | |
| 32 | 35 | 33 | 33 | 2.00E + 04 | 700 bp |
| 35 | 37 | 38 | 36 | 4.00E + 04 | |
| 40 | 40 | 43 | 41 | 6.00E + 04 | |
| 52 | 54 | 55 | 53 | 8.00E + 04 | |
| 63 | 69 | 69 | 67 | 1.00E + 03 | |
| 90 | 96 | 93 | 93 | 2.00E + 05 | |
| 115 | 118 | 119 | 117 | 4.00E + 05 | |
| 51 | 53 | 53 | 52 | 2.00E + 04 | un |
| 55 | 58 | 55 | 56 | 4.00E + 04 | |
| 60 | 64 | 62 | 62 | 6.00E + 04 | |
| 65 | 71 | 68 | 68 | 8.00E + 04 | |
| 69 | 75 | 75 | 73 | 1.00E + 05 | |
| 94 | 100 | 100 | 98 | 2.00E + 05 | |
| 120 | 130 | 125 | 125 | 4.00E + 05 | |
| 68 | 68 | 72 | 70 | 2.00E + 04 | 2,690 bp |
| 69 | 75 | 70 | 71 | 4.00E + 04 | |

TABLE 2-continued

Conductivity (µA) of DNA solutions over a range of frequencies

| replicates | | | | | |
|---|---|---|---|---|---|
| 1 | 2 | 3 | mean (µA) | frequency | size |
| 75 | 80 | 79 | 78 | 6.00E + 04 | |
| 76 | 77 | 80 | 77 | 8.00E + 04 | |
| 78 | 81 | 82 | 80 | 1.00E + 05 | |
| 102 | 104 | 111 | 106 | 2.00E + 05 | |
| 135 | 145 | 139 | 139 | 4.00E + 05 | |
| 134 | 137 | 138 | 136 | 2.00E + 04 | 50,000 bp |
| 138 | 142 | 152 | 144 | 4.00E + 04 | |
| 139 | 147 | 150 | 145 | 6.00E + 04 | |
| 142 | 143 | 153 | 146 | 8.00E + 04 | |
| 145 | 154 | 146 | 148 | 1.00E + 03 | |
| 151 | 154 | 163 | 156 | 2.00E + 03 | |
| 162 | 169 | 169 | 166 | 4.00E + 05 | |

TABLE 3

Conductivity (as µA and % response) of DNA solutions over a range of frequencies.

| 25 b | 700 bp | un | 2,690 bp | 50,000 bp | | |
|---|---|---|---|---|---|---|
| 21 | 33 | 52 | 70 | 136 | 2.00E + 04 | µA |
| 21 | 36 | 56 | 71 | 144 | 4.00E + 04 | |
| 22 | 41 | 62 | 78 | 145 | 6.00E + 04 | |
| 36 | 53 | 68 | 77 | 146 | 8.00E + 04 | |
| 55 | 67 | 73 | 80 | 148 | 1.00E + 05 | |
| 82 | 93 | 98 | 106 | 156 | 2.00E + 05 | |
| 114 | 117 | 125 | 139 | 166 | 4.00E + 05 | |
| 114 | 117 | 125 | 139 | 166 | 100% | |
| 18 | 28 | 42 | 50 | 82 | 2.00E + 04 | % response |
| 18 | 31 | 45 | 51 | 87 | 4.00E + 04 | |
| 19 | 35 | 50 | 56 | 87 | 6.00E + 04 | |
| 32 | 45 | 54 | 55 | 88 | 8.00E + 04 | |
| 48 | 57 | 58 | 58 | 89 | 1.00E + 05 | |
| 72 | 79 | 78 | 76 | 94 | 2.00E + 05 | |
| 100 | 100 | 100 | 100 | 100 | 4.00E + 05 | |

It is to be understood that various modifications may be made to the described embodiments within the ability of the skilled person. The scope of the invention should therefore only be determined by the claims.

What is claimed is:

1. A method for the estimation of a property of parameter of a nucleic acid material, said property or parameter being one to which the electrical conductivity of the nucleic acid material is related, which method comprises measuring the electrical conductivity of the nucleic acid material, and estimating from said measurement the property or parameter of the material by reference to a set relationship between electrical conductivity and said property or parameter.

2. Method according to claim 1, in which the parameter estimated is the concentration of nucleic acid in a solution thereof.

3. Method according to claim 2, in which the nucleic acid material consists predominantly of a simple species of nucleic acid.

4. Method according to claim 1, in which the property estimated is the molecular weight of a nucleic acid.

5. Method according to claim 4, which comprises measuring the conductivity of a solution containing nucleic acid using alternating current over a range of different frequencies.

6. Method according to claim 5, in which the molecular weight of the nucleic acid is estimated from the set relationship between molecular weight and the characteristic curve of electrical current/frequency response or a part thereof.

7. Method according to claim 6, in which the relationship is between molecular weight and the gradient of the response versus frequency curve.

8. Method according to any of claims 4 to 7, in which the property estimated is a overall indicator of molecular weight for a range of nucleic acid species.

9. Method according to claim 6, in which the apparatus has been precalibrated with respect to both the molecular weight/conductivity relationship and the concentration/conductivity relationship.

10. Method according to claim 1, in which the measurement is carried out with apparatus which has been precalibrated in accordance with the set relationship.

11. Method according to claim 1, in which conductivity is measured by measurement of alternating current flowing through a solution of the nucleic acid material.

12. Method according to claim 1, in which the nucleic acid is DNA.

13. An apparatus for the estimation of a property or parameter of nucleic acid material, said property of parameter being one to which the electrical conductivity of the nucleic acid material is related, which apparatus comprises a means for measuring the electrical conductivity of the nucleic acid material, and a means for estimating from said measurement the property or parameter of the material by reference to a set relationship between electrical conductivity and said property or parameter.

* * * * *